(12) United States Patent
Howe

(10) Patent No.: US 6,755,400 B2
(45) Date of Patent: Jun. 29, 2004

(54) FOAM GENERATOR, FOAMABLE PESTICIDE, AND METHOD

(76) Inventor: Michael F. Howe, 21 Woodland Crescent, Barrie, Ontario (CA), L4M 4Y8

( * ) Notice: Subject to any disclaimer, the term of this patent is extended or adjusted under 35 U.S.C. 154(b) by 212 days.

(21) Appl. No.: 10/044,883

(22) Filed: Oct. 26, 2001

(65) Prior Publication Data
US 2003/0080445 A1 May 1, 2003

(51) Int. Cl.[7] .................................................. B01F 3/04
(52) U.S. Cl. ............................ 261/121.1; 261/DIG. 26
(58) Field of Search ..................... 261/72.1, 77, 121.1, 261/DIG. 26

(56) References Cited

U.S. PATENT DOCUMENTS

| 2,212,598 A | * | 8/1940 | Hagist |
| 2,375,833 A | * | 5/1945 | Urquhart |
| 3,801,015 A | * | 4/1974 | Hayes |
| 3,946,947 A | * | 3/1976 | Schneider |
| 4,318,443 A | * | 3/1982 | Cummins |
| 4,606,477 A | * | 8/1986 | Spengler et al. |
| 4,693,854 A | * | 9/1987 | Yau |
| 5,775,591 A | * | 7/1998 | Fauci |
| 5,881,493 A | * | 3/1999 | Restive |
| 6,290,992 B1 | | 9/2001 | Magnuson-Hawkins |
| 6,308,866 B1 | * | 10/2001 | Hoang et al. |

* cited by examiner

Primary Examiner—Scott Bushey
(74) Attorney, Agent, or Firm—John D. Lister

(57) ABSTRACT

The airtight foamable liquid reservoir of a portable foam generator includes a pressurized air inlet and a discharge tube with one or more venturi openings. As a foamable liquid within the reservoir is discharged from the reservoir by the pressurized air through the discharge tube, pressurized air enters the discharge tube through the venturi opening(s) to create a fluid foam from the foamable liquid. For pest control, the foam generator may be utilized to foam and dispense a foamable pesticide that, preferably, includes a non-repellant, nonionic foaming agent adjuvant. The foamed pesticide may be introduced into walls and relatively inaccessible building locations as well as over the entrances of and into passages and habitats used by pests.

8 Claims, 3 Drawing Sheets

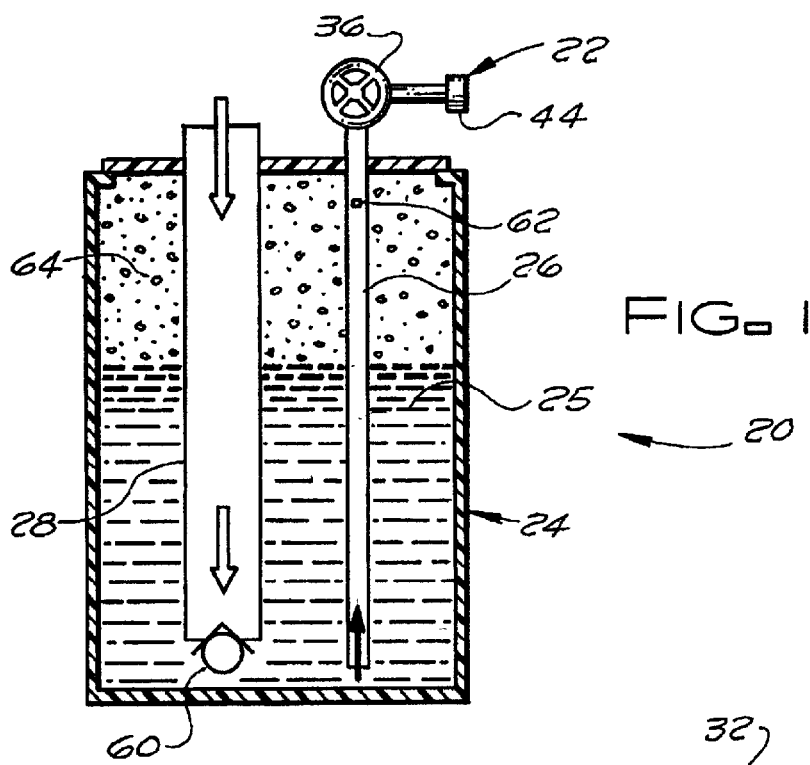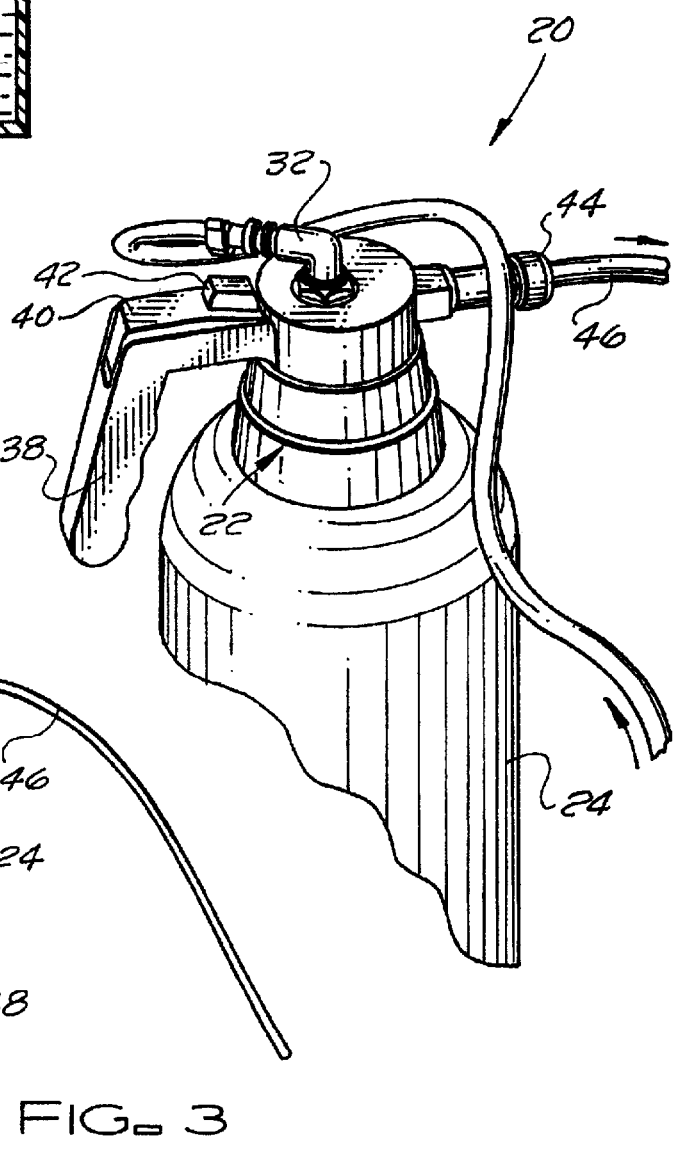
FIG. 1
FIG. 2
FIG. 3

FOAM GENERATOR, FOAMABLE PESTICIDE, AND METHOD

BACKGROUND OF THE INVENTION

The present invention relates to small lightweight portable hand held foam generation equipment, a foamable liquid non-repellant pesticide formulation that includes a non-repellant, nonionic adjuvant (foaming agent), and to a method of controlling pests with the foamable liquid non-repellant pesticide formulation. The foam generation equipment of the present invention is particularly well suited for introducing foamed pesticides into walls and other confined or enclosed building locations infested with pests and for dispensing foamed pesticides over the entrances of and into the passageways used by pests as well as into pest habitats. The light weight portable hand held foam generation equipment of the present invention also may be used for numerous other pest control applications, such as but not limited to, the application of herbicides and pesticides in the turf industry; the application of enzymes to drains in the sanitation industry; and the application of fungicides and pesticides in the tree and shrub industry. In addition to the various forms of pest control mentioned above, the light weight portable hand held foam generation equipment of the present invention may be used for many other applications where complete coverage of the surfaces, especially, though not limited to, the enclosed or relatively inaccessible surfaces of an enclosed space, cavity, or tubular structure with a coating and/or impregnating material is desired.

Conventional methods for controlling pest infestations, such as but not limited to termite infestations, include: the injection of pesticides beneath the slab and into the soil adjacent the perimeter of infested structures to create pesticide barriers; the location of pesticide containing bait stations in the soil adjacent the perimeter of infested structures, the fumigation of infested structures with pesticides; and the introduction of foamed pesticides into the walls and other enclosed spaces of infested structures such as disclosed in U.S. Pat. No. 6,290,992, issued Sep. 19, 2001. These methods for controlling pest infestations have been in use since at least the mid to late 1980's and, in the past, have utilized pest repellant pesticides.

SUMMARY OF THE INVENTION

In recent years non-repellant pesticides have been introduced into the pest control industry and utilized to control pests, such as termites, by the various methods discussed above. For these types of non-repellant pesticides to be most effective, the pests must move freely about the treated space, area or habitat and not recognize any repellant conditions. It is not necessary for the pests to feed directly on the pesticides or baits containing the pesticides. These non-repellant pesticides are lethal or injurious to pests through contact as well as through ingestion and/or transferal. When a pest comes in contact with the pesticide at least a few molecules of the pesticide adhere to the pest. These few molecules initiate a chemical and/or biological action within the pest that is injurious or lethal to the pest without any ingestion of the pesticide. In addition, pests contaminated with the pesticide then carry the pesticide back to the colony habitat or nest. Since many pests, such as termites, are social, other pests will groom the contaminated pests, and in turn, be groomed by other pests to spread the pesticide contamination throughout the colony. In addition, typically, pests killed by the pesticide will be eaten by other pests in the colony to further spread the pesticide throughout the colony. In this way, the entire colony, including the reproductive(s) of the colony, are destroyed.

Since the repeated and continued passage of a number pests through the treated spaces or areas for a period of time is desired so that numerous pests quickly convey the non-repellant pesticide back to and/or through a colony nest or habitat to spread the pesticide throughout the colony, for this type of non-repellant pesticide to work most effectively when applied in the form of a foam, not only the pesticide but the foamable liquid pesticide formulation made from the pesticide should be non-repellant. In other words, any adjuvant added to the non-repellant pesticide to form a foamable liquid pesticide formulation should also be non-repellant. Otherwise, if the adjuvant added to the non-repellant pesticide is to a greater or lesser extent repellant, a pesticide that in of itself is non-repellant, applied as a foam becomes repellant to the degree that the adjuvant is repellant thereby making the pesticide less effective or possibly ineffective.

In addition, the adjuvant added to a non-repellant pesticide to form a foamable liquid pesticide formulation should be nonionic so that the pesticide molecules in the coating, film or layer left after the foam breaks down are not held by the adjuvant in the coating, film or layer, but are easily released upon contact to contaminate the pests being controlled. Accordingly, for non-repellant pesticides applied as foams to be most effective, the adjuvant of the foamable liquid pesticide formulations used to form the pesticide foams must be both non-repellant and nonionic. To applicant's knowledge, the adjuvants added to these non-repellant pesticides to form foamable liquid pesticide formulations have not contained adjuvants that are non-repellant and/or nonionic. Accordingly, there has been a need to provide a more effective method of pest control through the use of non-repellant pesticides in foamable formulations that do not include other ingredients that will repel the pests or retain the pesticide molecules in the formulation.

The small lightweight portable hand held foam generation equipment, the foamable liquid pesticide formulation with its non-repellant and nonionic adjuvant, and the method of controlling pests with the foamable liquid pesticide formulation of the present invention provide a solution to the above discussed problems of the prior art. As used herein the term "pesticide" includes but is not limited to termiticides, fungicides, herbicides, growth regulators, particles of bait treated or impregnated with agents that destroy pests, and other agents used to destroy pests.

The small lightweight portable hand held foam generation equipment of the present invention may be easily and readily used by both home handymen/women (do-it-your-selfers) and commercial contractors to foam various foamable liquids at different volumetric expansion ratios between 2 to 1 and 25 to 1 with volumetric expansion ratios between 6 to 1 and 20 to 1 or between 15 to 1 and 20 to 1 being typical of the volumetric increases selected for most applications. In addition to being inexpensive, readily portable, easy to use, and having a high foam discharge rate, with its uniquely simplified construction, the foam generation equipment of the present invention is easy and inexpensive to maintain.

The hand held foam generator of the present invention includes an airtight reservoir for containing a foamable liquid and is pressurized with air through an air pump that is integral with the hand held foam generator or a source of pressurized air connected by air supply lines to the reservoir of the hand held foam generator. In one preferred embodiment, the foam generator includes a foam dispensing assembly, e.g. a conventional foam application gun, mounted directly on the reservoir and a unique discharge tube that extends from the foam dispensing assembly down into the reservoir for discharging the foamable liquid from the reservoir as a fluid foam through the foam dispensing assembly. Preferably, the discharge tube is both flexible and weighted, at or adjacent the bottom of the tube, to cause the discharge tube to move in any direction that the foamable liquid moves when the foam generation equipment is tilted. Thus, when the hand held foam generation equipment of the present invention is moved, turned or tilted in any of numerous directions while in use, the lower end of discharge tube will continue to be immersed in the foamable liquid in the reservoir and continue to withdraw the foamable liquid from the reservoir.

The discharge tube has one or more venturi openings, above a maximum foamable liquid fill line of the reservoir, for introducing pressurized air within the reservoir into the discharge tube. Although it is preferred for ease of use to have a maximum foamable liquid fill line marking on the reservoir to aid the user in filling the reservoir to its maximum selected capacity, as used herein, the term "maximum foamable liquid fill line of the reservoir" does not have to be an actual marking on the reservoir, but is a level at or below which a foamable liquid should be maintained in the reservoir to assure that the foamable liquid does not cover a venturi opening in the discharge tube. The pressurized air introduced into the discharge tube through the one or more venturi openings mixes with the foamable liquid as the foamable liquid is discharged from the reservoir by the pressurized air through the discharge tube to form a fluid foam. The fluid foam is dispensed by the foam dispensing assembly and is spread by a process called "stacking" or otherwise flows over and into the space or spaces being treated to fully wet, impregnate and/or coat all of the surfaces within the space or spaces including porous surfaces, cracks in the surfaces, joints, and passageways and the entrances of passageways leading into or out of the space or spaces.

For certain applications where the foam generation equipment is set up to produce a foam from a particular foamable liquid formulation at a particular volumetric expansion ratio and increased volumetric expansion ratios are desired to form a dryer foam for a portion of the application or for a different application, a foam expansion chamber may be added to the foam dispensing assembly to further mix the air with the foam coming from the reservoir to obtain the desired increase in the volumetric expansion of the foam. The particular foam expansion chamber added to the foam dispensing assembly is selected to provide the additional volumetric expansion desired. While conventional foam expansion chambers utilizing stainless steel wool or a form 3M Scotch brand brite pad may be attached to the foam dispensing assembly, preferably, the foam expansion chamber includes an inlet tube with one or more venturi openings therein to create a vortex action within the foam as the foam passes through the chamber. In addition, a foam expansion chamber may be utilized to maintain the same volumetric expansion ratio at lower than normal operating pressures, e.g. operating pressures below 15 pounds per square inch gauge.

The foamable liquid non-repellant pesticide formulation of the present invention includes a pesticide that is non-repellant to a selected type of pest and a foaming agent or surfactant adjuvant, blended or mixed with the non-repellant pesticide, that is non-repellant to the particular pest being treated and, preferably, also nonionic to facilitate the contamination of the pests with molecules of the pesticide.

With respect to pest control, the hand held foam generation equipment of the present invention enables new procedures to be utilized in the treatment of various pests with foam pesticides. In addition to termites, pests, such as but not limited to carpenter ants, cockroaches, bees, wasps, hornets, fire ants and drain flies, have traditionally been controlled through the injection of liquid pesticides into soil, liquid pesticides sprayed onto or into pest habitats, the fumigation of spaces with gas or dust pesticides, or the inclusion of pesticides in baits. With the small, lightweight, portable, high foam output foam generation equipment of the present invention, these and other pests can also be controlled through the use of foam pesticides and especially through the use of foam pesticides formed from the foamable non-repellant liquid pesticide formulation of the present invention.

For example, the small, lightweight, portable, high foam output foam generation equipment of the present invention enables pest control workers, unencumbered by heavy and awkward to use equipment, to easily and quickly apply fluid foam pesticides, preferably formed from the foamable non-repellant liquid pesticide formulation of the present invention, to numerous fire ant colonies spread out over a large area. In addition, by applying the fluid foam pesticide to the ground in an area surrounding the main entrance(s) to the colony before applying the foam pesticide to the main entrances, ants will not be able to move across the ground to attack the pest control worker and auxiliary entrances used by the colony to attack an intruder such as the pest control worker can be temporarily sealed by the foam to prevent the ants from attacking the pest control worker. After the foam breaks down, a coating, film or layer of pesticide covers the entrances to and at least upper portions of passageways down into the colony nest and the ground surrounding the nest. When the foamable non-repellant liquid pesticide formulation of the present invention is used to form the foam pesticide, ants continue to move through the passageways and over the ground treated with the pesticide and make contact with the pesticide that is transferred by such contact to their bodies. The pesticide is then spread throughout the colony in a manner similar to that discussed above in connection with termites.

In another example of the versatility of the small, lightweight, portable, high foam output foam generation equipment of the present invention, the foam generation equipment of the present invention enables pest control workers, unencumbered by heavy and awkward to use equipment, to easily and quickly apply foam pesticides to bee hives, wasp nests, hornet nests, etc., even when these hives or nests are located in relatively inaccessible locations. As an aid, one or more lightweight, rigid or semi-rigid dispensing tubes, each from one to two meters long, or a telescoping dispensing tube of two or more sections, each from one to two meters long, can be attached to the foam dispensing assembly to deliver the fluid foam pesticide to hives or nests high above the ground or otherwise not readily accessible. The application of the fluid foam pesticide to the hive or nest during treatment temporarily seals the entrances to the hive or nest thereby protecting the pest control worker during the application of the pesticide. After the foam breaks down, a coating, film or layer of pesticide covers not only the entrances to and at least outer portions of passageways leading into the hive or nest but also the outer surfaces of the hive or nest. When the non-repellant foam pesticide of the present invention is used, bees, wasps, hornets or other pests continue to move through the passageways and over the hive or nest and contact the pesticide that is transferred by such contact to their bodies. The pesticide is then spread throughout the colony in a manner similar to that discussed above in connection with termites.

While the portable hand held foam generation equipment of the present invention is especially well suited for use in pest control applications, it should be noted that the portable hand held foam generation equipment of the present invention is also very well suited for many other applications where light weight, portable, easy to use and manipulate, hand held foam generators would be required or desired. For example, the foam generation equipment of the present invention may be used by a home handyman/woman or a commercial contractor or business: to apply a foam cleaner to the tires or the engine of a vehicle or aircraft, to a apply an anti-bacterial foam to the walls of a meat packing room, and to apply foams in many other applications where the application of a material to a surface, exposed or relatively inaccessible, is desired to coat, impregnate or otherwise treat the surface.

BRIEF DESCRIPTION OF THE DRAWINGS

FIG. 1 is a schematic vertical cross section through the foam generation equipment of the present invention.

FIG. 2 is a perspective view of the reservoir of the hand held foam generation equipment of the present invention.

FIG. 3 is a partial perspective view of an embodiment of the hand held foam generation equipment of the present invention that utilizes an external source of pressurized air.

DESCRIPTION OF THE PREFERRED EMBODIMENT

Figure 4:
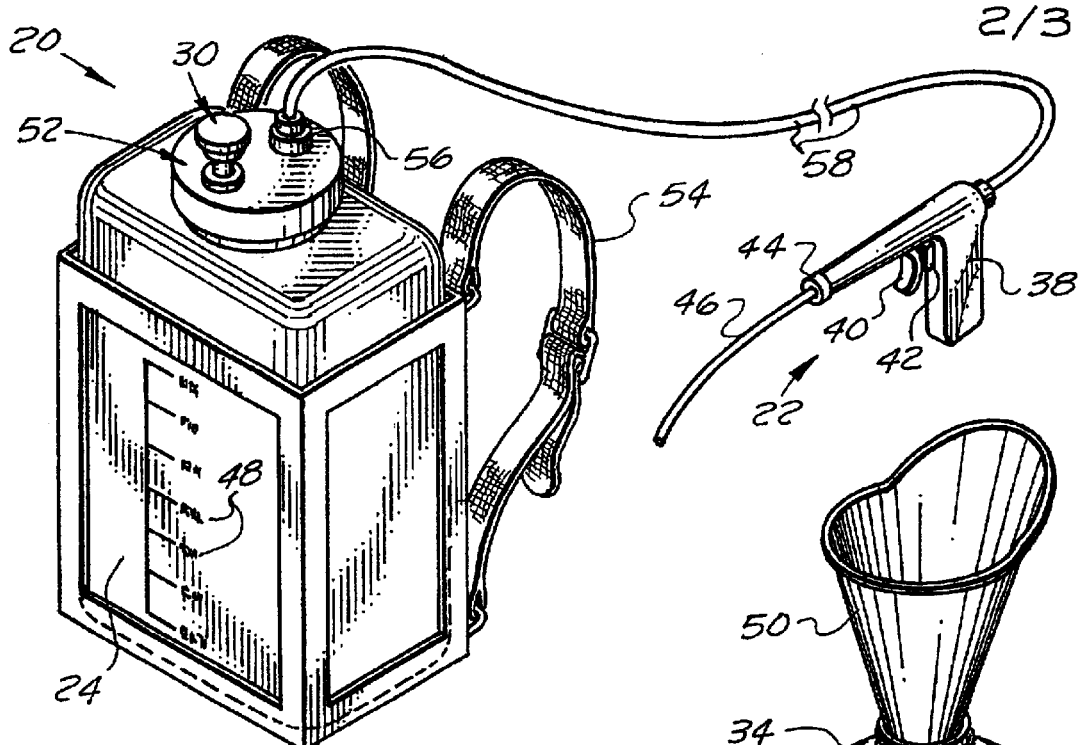
FIG. 4 is a perspective view of an embodiment of the hand held foam generation equipment of the present invention where the reservoir is carried by the foam dispensing assembly and includes a hand-operated air pump to provide a source of pressurized air.

As schematically shown in FIG. 1 and FIGS. 2 to 7, the small, lightweight, portable, high foam output foam generation equipment 20 of the present invention includes a foam dispensing assembly 22, a reservoir 24 for containing a foamable liquid 25, a discharge tube 26 for withdrawing a foamable liquid from the reservoir 24 and discharging a fluid foam formed in the discharge tube through the foam dispensing assembly 22, and a pressurized air inlet tube 28 for introducing pressurized air into the reservoir 24. The pressurized air inlet tube 28 is part of a hand-operated air pump 30 incorporated into the foam generation equipment 20 or is provided with a conventional coupling 32 for connecting the reservoir to a source (not shown) of pressurized air.

In a preferred form, the foam dispensing assembly 22 forms a closure that is threaded onto the inlet opening 34 used to fill the reservoir 24 with a foamable liquid or is otherwise detachably mounted to the top of the reservoir 24. When the foam generation equipment 20 is in use, the foam dispensing assembly 22 forms an airtight seal with the inlet opening 34. The foam dispensing assembly 22 includes a conventional control valve 36 for starting, stopping and regulating the flow of fluid foam from the reservoir 24. As shown in FIGS. 2, 3 and 4, in a preferred form, the foam dispensing assembly 22 includes a handle 38 that may be easily gripped by the user to carry and manipulate the foam generation equipment 20. The control valve 36 is actuated by a trigger 40 that includes a trigger lock 42 for holding the control valve 36 in an on or off position. The inlet side of the control valve 36 is connected to the downstream end of the discharge tube 26 and receives fluid foam from the reservoir 24 through the discharge tube 26. The outlet side of the control valve 36 is connected through a tube to a conventional coupling mechanism 44 for detachably securing various dispensing tips or devices 46, such as nozzles of various configurations, flexible tubing, semi-rigid tubing or rigid tubing sections, and telescoping tubing sections to the foam dispensing assembly 22.

Figure 5:
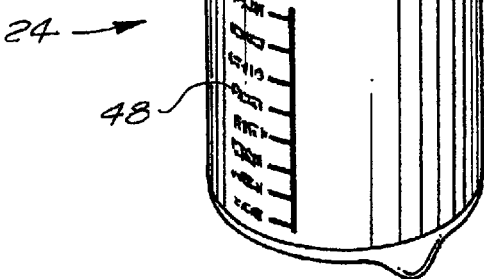
FIG. 5 is a perspective view of an embodiment of the hand held foam generation equipment of the present invention where the reservoir is carried on the workers back and includes a hand-operated air pump to provide a source of pressurized air.

Preferably, as shown in FIG. 5., the reservoir 24 is a transparent tank with a measuring scale 48 so that the worker can accurately blend a foamable liquid formulation in the reservoir, fill the reservoir with the desired quantity of foamable liquid, not overfill the reservoir, and monitor the quantity of foamable liquid remaining in the reservoir during use of the foam generation equipment 20. The opening 34 in the top of the reservoir 24 is sized to easily accept a funnel 50 for introducing the ingredients of a foamable liquid formulation into the reservoir for blending, for filling the reservoir with a pre-blended foamable liquid formulation, and for receiving the discharge tube 26 and pressurized gas inlet tube 30 that extend down into the reservoir from the foam dispensing assembly 22 or a closure assembly 52.

In the embodiments of the invention shown in FIGS. 2 and 3 where the foam dispensing assembly 22 is mounted directly on the reservoir 24, the reservoir typically has a capacity of about 1.0 to 3.0 liters and the foam generation equipment 20, with the reservoir empty, weighs about 0.5 kilograms. The capacity of the reservoir 24 may be less, but for most applications a capacity of at least 1.0 to 3.0 liters is desirable to avoid the necessity of frequent reservoir refills. The capacity of the reservoir 24 may be greater than 3.0 liters. However, for most applications, a reservoir capacity between 1.0 and 3.0 liters is sufficient and with an increase in the capacity of the reservoir 24 beyond 3.0 liters, the weight of the foam generation equipment, when the reservoir is filled with a foamable liquid, starts to become a factor.

For foaming applications such as commercial foaming applications where additional reservoir capacity may be desired, e.g. reservoir capacities up to about 20 liters, the reservoir 24 can be carried on the worker's back by a harness 54 secured over the worker's shoulders. In embodiments of the invention where the reservoir 24 is carried by the worker on his/her back, such as the foam generation equipment 20 shown in FIG. 4, the inlet opening 34 for filling the reservoir is closed by the closure assembly 52. In service, the closure assembly 52 is threaded onto the inlet opening 34 to form an airtight seal. The closure assembly 52 includes a discharge tube 26 and although the reservoir may be connected through the closure assembly 52 to an external source of pressurized air, typically, the closure assembly 52 includes a hand-operated air pump 30. The discharge tube 26 includes a coupling 56 to connect the discharge tube 26 through a tube 58 to the foam dispensing assembly 22 (e.g. a conventional dispensing gun with a control valve 36 is actuated by a trigger 40 and includes a trigger lock 42 for holding the control valve 36 in an on or off position) that can be held and easily manipulated by the worker.

As discussed above, the pressurized air inlet tube 28 is either the tube of a conventional hand-operated air pump 30 or a tube with a conventional pneumatic coupling 32 for coupling the inlet tube 28 to an external source of pressurized air such as but not limited to the pressurized air supply line from a conventional air compressor. In service, the reservoir 24 is preferably pressurized to about 40-psi gauge (pounds per square inch gauge). However, the foam generation equipment 20 can function at pressures from 15-psi to 40-psi gauge and above. At pressures within the reservoir 24 below 15-psi gauge the foam discharge rate from the foam generation equipment 20 is generally lower than desired for most applications. Pressures within the reservoir 24 above 40-psi gauge are not required to attain desired foam discharge rates from the foam generation equipment 20. When the reservoir 24 is connected to an external source of pressurized air, such as an air compressor, the pressure within the reservoir 24 is normally maintained at about 35-psi to 40-psi gauge and a pressure relief valve on the air compressor keeps the pressure within the reservoir 24 from exceeding 40-psi gauge. When a hand-operated air pump 30 is utilized to pressurize the reservoir 24 and the air pressure drops within the reservoir 24 during use, the worker periodically pumps the hand-operated air pump to increase the pressure within the reservoir to a desired level.

The outlet for the pressurized air inlet tube 28 is provided with a conventional check valve 60 to prevent the foamable liquid within the reservoir 24 from backing up into the pressurized air inlet tube 28. Preferably, the outlet for the pressurized air inlet tube 28 is located adjacent, but spaced above, the bottom of the reservoir 24 so that the pressurized air emitted into the reservoir from the pressurized air inlet tube 28 flows up through the foamable liquid within the reservoir to commence the mixing of the air with the foamable liquid.

Figure 6:
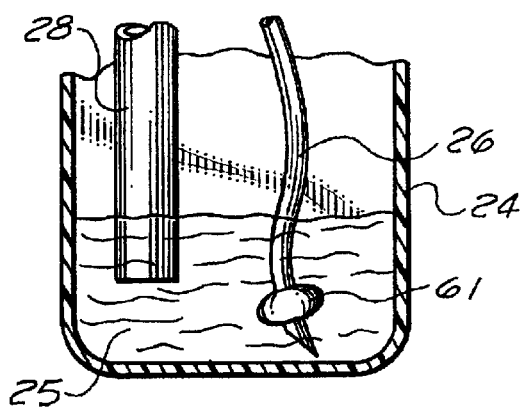
FIG. 6 is a partial vertical cross section through a lower portion of a reservoir of the foam generation equipment of the present invention, with the equipment and reservoir in an upright position, showing a lower portion of a flexible, weighted discharge tube extending into a foamable liquid within the reservoir.
Figure 7:
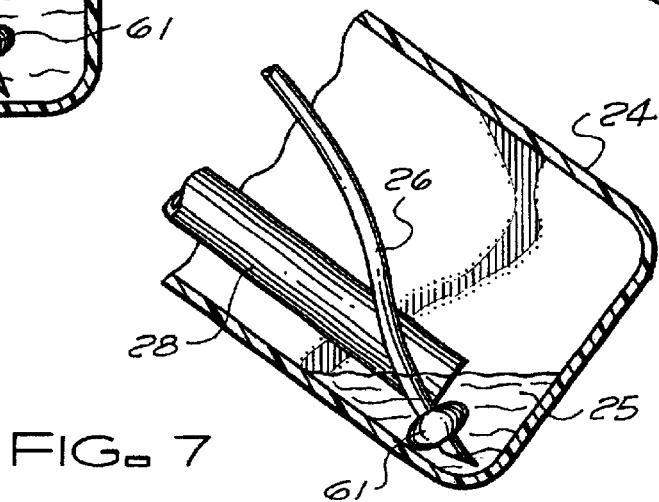
FIG. 7 is a partial vertical cross section through a lower portion of a reservoir of the foam generation equipment of the present invention, with the equipment and reservoir tilted, showing a lower portion of a flexible, weighted discharge tube still extending into a foamable liquid within the reservoir.

The discharge tube 26 has an inlet opening at its lower end that is located adjacent but above the bottom of the reservoir 24. While the discharge tube 26 may be rigid, preferably and as shown in FIGS. 6 and 7, the discharge tube is flexible and provided with a weight 61 located at or adjacent the lower end of the discharge tube. Preferably, the lower end of the discharge tube 26, forming the inlet opening of the discharge tube 26, is inclined at an angle of other than 90° to the longitudinal axis of the discharge tube to help keep the inlet opening of the discharge tube from becoming clogged or blocked. In addition, the weight 61 is sized, e.g. in diameter, and located relative to the inlet opening of the discharge tube 26 to keep the inlet opening of the discharge tube out of contact with a sidewall of the reservoir when the reservoir is tilted as shown in FIG. 7.

The discharge tube 26 includes one or more venturi openings 62 that are located in the discharge tube 26 above the maximum fill line for foamable liquid 25 within the reservoir 24 so that the venturi opening or openings are not covered by the foamable liquid 25 within the reservoir. Thus located, the one or more venturi openings 62 in the discharge tube 26 are positioned in a pressurized gas space 64 above the foamable liquid in the reservoir. As the foamable liquid 25 is forced out of the reservoir 24 through the discharge tube 26 and the dispensing assembly 22 by the pressurized air within the reservoir, the flow of the foamable liquid 25 past the one or more venturi openings 62 in the discharge tube creates a low-pressure zone within the discharge tube at each venturi opening. Each low-pressure zone draws the pressurized air from the space 64 in the reservoir above the foamable liquid 25 into the discharge tube 26 where the pressurized gas mixes with the foamable liquid 25 to form a fluid foam that is discharged from the reservoir through the discharge tube 26 into the foam dispensing assembly 22.

Preferably, the total cross sectional area of the venturi opening or openings 62 in the discharge tube 26 is between 0.01% and 50% of the total cross sectional area of the internal transverse cross section of the discharge tube 26, e.g. two $\frac{1}{32}$ of an inch diameter venturi openings in a discharge tube having an internal diameter of $\frac{1}{8}$ of an inch. If the venturi opening or openings 62 are too small, insufficient quantities of pressurized air are introduced into the discharge tube 26 to effectively foam the foamable liquid 25 passing through the discharge tube. If the venturi opening or openings 62 are too large, the pressurized air within the reservoir will not force the foamable liquid 25 into the inlet opening of the discharge tube 26. Instead, when the valve 36 is opened, the pressurized air within the reservoir 24 will take the path of least resistance and escape through the venturi opening and out through the dispensing assembly 22 leaving the foamable liquid 25 unfoamed within the reservoir.

In a preferred arrangement, that appears to provide a most efficient foam formation and method of forming two venturi openings 62 in the discharge tube, two venturi openings 62 are diametrically opposed to and aligned with each other in the discharge tube 26. Where there is more than one venturi opening, the venturi openings 62 may be of equal or unequal size, may be on the same level or different levels, and/or may be opposed as in the preferred arrangement or off set from each other at various angles, e.g. 90°.

Where the foam generation equipment 20 is set up to produce a particular volumetric expansion ratio for a particular foamable liquid formulation and increased volumetric expansion ratios are desired for a portion of the application or for a different application, a foam expansion chamber 66 may be added to the foam dispensing assembly 22 to further mix the air with the fluid foam discharged from the discharge tube 26 and obtain the desired additional volumetric expansion of the fluid foam coming from the discharge tube 26. The particular foam expansion chamber 66 added to the foam dispensing assembly 22 is selected to provide the additional volumetric expansion or increase in foam volume desired. The foam expansion chamber 66 is secured by a conventional airtight coupling to the foam dispensing assembly between the valve 36 in the foam dispensing assembly 22 and any dispensing tips 46 attached to the foam dispensing assembly.

Figure 8:
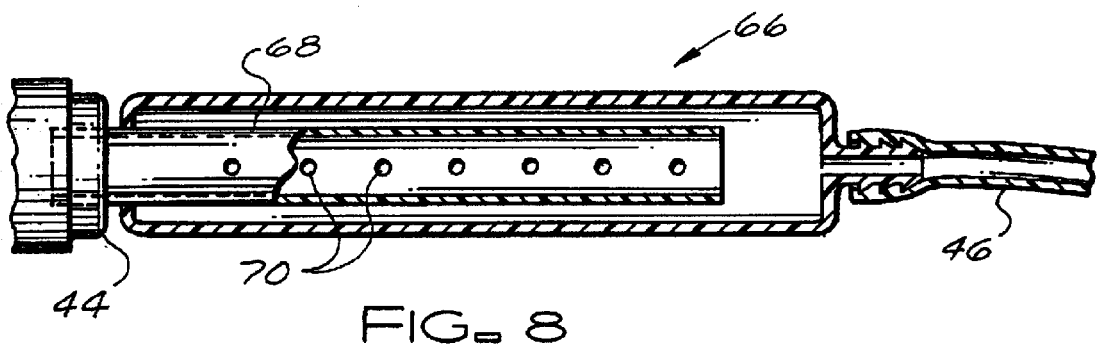
FIG. 8 is a schematic longitudinal cross section through a first optional foam expansion chamber that may be connected to the foam dispensing assembly of the foam generation equipment of the present invention.
Figure 9:
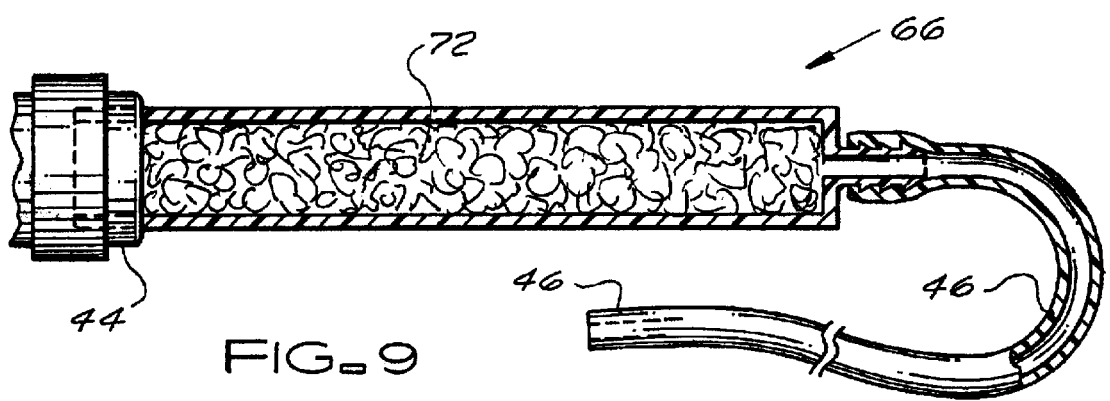
FIG. 9 is a schematic longitudinal cross section through a second optional foam expansion chamber that may be connected to the foam dispensing assembly of the foam generation equipment of the present invention.
Figure 10:
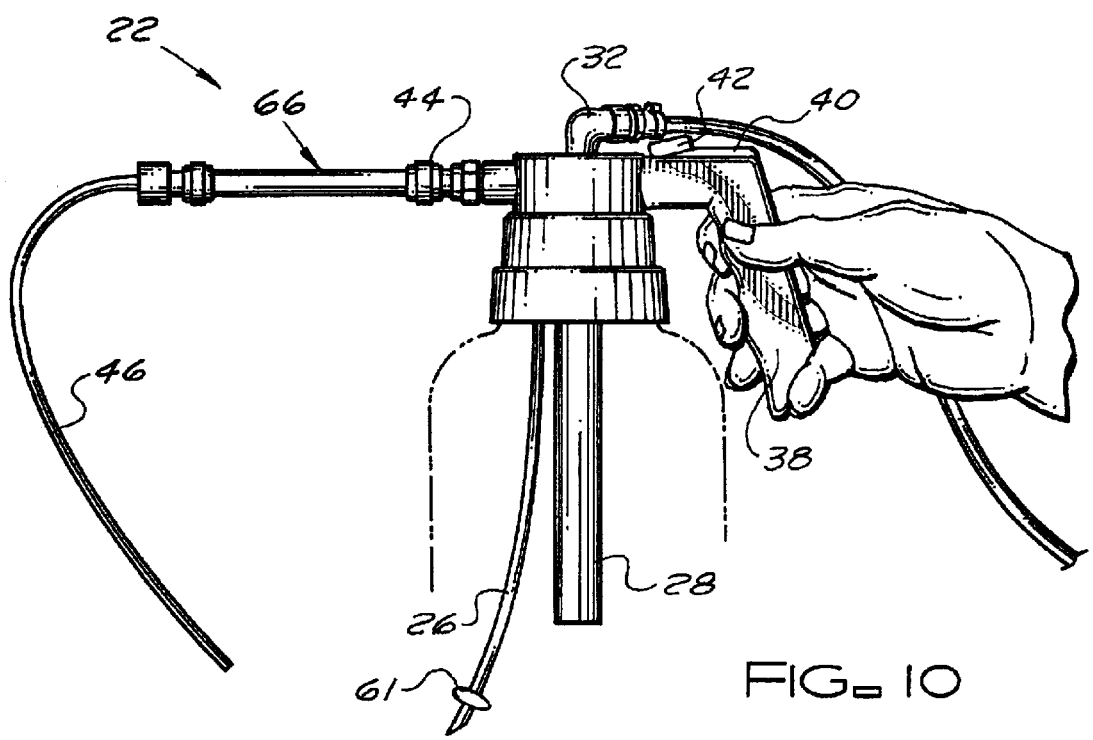
FIG. 10 is a side elevation view of a dispensing assembly of the present invention with an expansion chamber attached to the dispensing assembly.

FIGS. 8, 9 and 10 show foam expansion chambers 66 and a dispensing assembly 22 with a foam expansion chamber 66 mounted on the dispensing assembly. The foam expansion chamber 66 shown in FIG. 8 includes an inlet tube 68 extending into and only partially through the expansion chamber 66 for introducing the fluid foam from the discharge tube 26 into the expansion chamber. The foam expansion chamber 66 has a greater interior transverse cross sectional area than the inlet tube 68 whereby fluid foam within and passing through the chamber 66 completely surrounds the inlet tube. The inlet tube is provided with one or more venturi openings 70 along the length the tube, preferably about six, to create a vortex action within fluid foam as the fluid foam passes through the foam expansion chamber. As the fluid foam is introduced into the foam expansion chamber 66 through the inlet tube 68, the flow of the fluid foam past the one or more venturi openings 70 draws the fluid foam in the foam expansion chamber surrounding the inlet tube back into the tube and creates a vortex action within the foam expansion chamber to further agitate or mix the air with the fluid foam coming from the discharge tube 26 and increase the volume of the fluid foam dispensed. The foam expansion chamber 66 of FIG. 9 houses or contains wool 72, e.g. stainless steel wool or a form of 3M Scotch brand brite pads, within the foam expansion chamber. As the fluid foam from the discharge tube 26 passes through the wool within the expansion chamber, the fluid foam and air are further agitated and mixed to increase the volume of the fluid foam dispensed. Typically, the internal diameters of the line leading from the control valve 36 into the expansion chamber 36 and the dispensing tip 46 leading from the expansion chamber will be about ⅛ of an inch while the internal diameter of the expansion chamber will be about ¼ of an inch.

The foamable liquid non-repellant pesticide formulation of the present invention includes a non-repellant pesticide and a foaming agent or surfactant adjuvant, blended or mixed with the non-repellant pesticide. Both the pesticide and the adjuvant are non-repellant to the particular pest being treated. Preferably, the adjuvant is also nonionic to facilitate the contamination of the pests with molecules of the pesticide. The preferred adjuvant of the present invention includes the following ingredients in the following amounts in percentage by weight that are blended into about one kilogram of water:

| | | |
|---|---|---|
| 1. | Water | one kilogram |
| 2. | Coconut Fatty Acid | 20–30 |
| 3. | Glycol Ether EB | 10–20 |
| 4. | Sodium Lauryl Sulfate | 5–20 |
| 5. | Ethoxylated Fatty Acids and Mineral Oils | 5–20 |
| 6. | Hexylene Glycol | 0.5–20 |
| 7. | Denatured Alcohol | 0.001–20 |
| 8. | Lorol C8–10 | 0.01–15 |
| 9. | Disodium Laureth Sulfosuccinate | 0.01–10 |

The adjuvant is prepared as follows:
1. Ingredients 1, 2 and 3 are mixed for about two minutes or until a uniform blending of the ingredients is achieved.
2. Ingredients 4, 5 and 6 are then added to the previously blended ingredients 1 to 3 and mixed with the previously blended ingredients for two minutes or until a uniform blending of the ingredients is achieved.
3. Ingredients 7, 8 and 9 are then added to the previously blended ingredients 1 to 6 and mixed with the previously blended ingredients for five minutes or until a uniform blending of the ingredients is achieved.

The adjuvant has a specific gravity of about 1.020 to 1.026 and a pH (in a 2% solution) of 7.0. The coconut fatty acid, sodium lauryl sulfate, hexylene glycol and denatured alcohol may be obtained from Canada Colours of Don Mills, Ontario, Canada. The glycol ether EB may be obtained from Asland of Mississauga, Ontario, Canada. The ethoxylated fatty acids and mineral oils may be obtained from Uniqema of Brantford, Ontario, Canada under the trade designation Atplus 452. The lorol C8–10 may be obtained from Cognis of Mississauga, Ontario, Canada.

The foamable liquid non-repellant pesticide formulations of the present invention include: a non-repellant pesticide; water (either previously blended with the non-repellant pesticide or added to a non-repellant pesticide concentrate in an amount specified by the non-repellant pesticide manufacturer) and a sufficient amount of the non-repellant, nonionic adjuvant of the present invention to cause the resultant foamable liquid non-repellant pesticide formulation to have a volumetric expansion ratio, when foamed, of between 2 to 1 and 25 to 1 and normally between 6 to 1 and 20 to 1 or between 15 to 1 and 20 to 1.

When used for termite control, the foamable liquid non-repellant pesticides of the present invention typically include: a non-repellant termiticide, such as a non-repellant termiticide with imidacioprid or fipronil as the active ingredient; water (either previously blended with the non-repellant termiticide or added to a non-repellant termiticide concentrate in an amount specified by the manufacturer) and a sufficient amount of the non-repellant, nonionic adjuvant of the present invention to cause the resultant foamable liquid non-repellant termiticide formulation, to have a volumetric expansion ratio, when foamed, of between 2 to 1 and 25 to 1 and normally between 6 to 1 and 20 to 1 or between 15 to 1 and 20 to 1. A non-repellant termiticide with imidacioprid as the active ingredient may be obtained from Bayer of Kansas City, Mo., USA, under the trade designation "PREMISE". A non-repellant termiticide with fipronil as the active ingredient may be obtained from Bayer of Kansas City, Mo., USA, under the trade designation "TERMIDOR". The foamable liquid non-repellant pesticides of the present invention may be preblended for use by the home handyman/woman or may be blended in the field by the home handyman/woman or a professional pest control contractor.

Typically, to form a foamable liquid, such as but not limited to a foamable liquid pesticide formulation, with a volumetric expansion ratio between 6 to 1 and 20 to 1, a foamable liquid blended in accordance with the present invention will require between 5 and 30 milliliters of the adjuvant of the present invention to be added to 1 liter of the solution or mixture to be foamed. However, the specific amount of adjuvant to be added to a particular solution or mixture, such as a pesticide solution or mixture, to obtain a desired volumetric expansion ratio for the foamable liquid may be determined by performing the following calibration procedure. Fluid foam made from the foamable liquid formulation of the present invention is dispensed into a container of known volume filling the container. After the fluid foam breaks down into a liquid, the volume of the liquid in the container is measured. The volume of the liquid relative to the volume of the container equals the volumetric expansion ratio. Should the ratio be other than that desired, the amount of adjuvant of the present invention added to the solution or mixture may be adjusted and the procedure repeated until the desired volumetric expansion ratio is obtained.

In describing the invention, certain embodiments have been used to illustrate the invention and the practices thereof. However, the invention is not limited to these specific embodiments as other embodiments and modifications within the spirit of the invention will readily occur to those skilled in the art on reading this specification. For example, as mentioned in the summary of the invention, the foam generation equipment of the present invention may be used by a home handyman/woman or a commercial contractor or business: to apply a foam cleaner to the tires or the engine of a vehicle or aircraft, to a apply an antibacterial foam to walls of a meat packing room, and to apply foams in many other applications where the application of a material to a surface, exposed or relatively inaccessible, is desired to coat, impregnate or otherwise treat the surface. Also for certain applications a pressurized gas other than air may be used to pressurize the reservoir 24 and mix with a particular foamable liquid. Thus, the invention is not intended to be limited to the specific embodiments disclosed, but is to be limited only by the claims appended hereto.

What is claimed is:

1. A portable foam generator to be carried by a person for applying a fluid foam pesticide, comprising:

an airtight reservoir for containing a foamable liquid pesticide; the reservoir having an upper end, a lower end, and a foamable liquid pesticide maximum fill line intermediate the upper end and the lower end of the reservoir;

a pressurizing means, other than a hand-operated air pump, for introducing pressurized air into the reservoir; the air pressurizing means complaining a source of maintains an air pressure within the reservoir of at least 35 psi gauge; the air inlet tube of the pressurizing means discharging the pressurized air into the reservoir below the foamable liquid pesticide maximum fill line and including a check valve to prevent the foamable liquid pesticide from flowing back into a pressurized air outlet of the air inlet tube;

a discharge tube for foaming the foamable liquid pesticide and discharging fluid foam pesticide made from the foamable liquid the from the reservoir, the discharge tube being flexible and weighted adjacent an inlet opening at the bottom end of the discharge tube so that in use the discharge tube continues to be immersed within the foamable liquid pesticide within the reservoir when the reservoir of the portable foam generator is tilted; the discharge tube having venturi opening means above the foamable liquid pesticide maximum fill line for introducing pressurized air within the reservoir into the discharge tube to mix with the foamable liquid pesticide as the foamable liquid pesticide passes through the discharge tube, to form the fluid foam pesticide that is discharged from the reservoir by the pressurized air through the discharge tube; the total cross sectional area of the venturi opening means in the discharge tube being between 0.01% and 50% of the total transverse cross sectional area of the tubular passage in the discharge tube; and a hand-held foam dispensing means connected to the discharge tube for controlling the discharge of and dispensing of the fluid foam pesticide delivered from the discharge tube.

2. The portable foam generator according to claim 1, wherein:

the venturi opening means comprises a single venturi opening in the discharge tube.

3. The portable foam generator according to claim 1, wherein:

the venturi opening means comprises a plurality of venturi openings in the discharge tube.

4. The portable foam generator according to claim 1, wherein:

the venturi opening means comprises two diametrically opposed and aligned venturi openings in the discharge tube.

5. The portable foam generator according to claim 1, wherein:

the hand-held foam dispensing means is mounted directly on the reservoir so that in use the reservoir is carried with the hand-held foam dispensing means.

6. The portable foam generator according to claim 1, wherein:

the reservoir is mounted in a harness to be carried on a person's back; and the hand-held foam dispensing means is connected to the reservoir through a fluid foam delivery line.

7. The portable foam generator according to claim 1, wherein:

the hand-held foam dispensing means includes a foam expansion chamber for further mixing of air in the fluid foam pesticide delivered from the discharge tube with the fluid foam pesticide delivered from the discharge tube to effect an increase in a volumetric expansion of the fluid foam pesticide.

8. The portable foam generator according to claim wherein:

the foam expansion chamber has an interior transverse cross section; the expansion chamber has a fluid foam inlet tube for introducing the fluid foam pesticide from the reservoir into the foam expansion chamber, the fluid foam inlet tube has a smaller outer transverse cross section than the interior transverse cross section of the expansion chamber; a portion of the fluid foam inlet tube within the foam expansion chamber has at least one venturi opening in a tubular sidewall of the fluid foam inlet tube whereby as the fluid foam pesticide passes from the reservoir into the expansion chamber through the fluid foam inlet tube a portion of the fluid foam pesticide within the foam expansion chamber is drawn back into the fluid foam inlet tube to further agitate the fluid foam pesticide and further increase the volumetric expansion of fern the fluid foam pesticide dispensed.

* * * * *